United States Patent
Livesey et al.

(10) Patent No.: US 6,194,136 B1
(45) Date of Patent: Feb. 27, 2001

(54) CRYOPROTECTIVE SOLUTIONS COMPRISING DMSO, PG, 2,3-BUTANEDIOL, RAFFINOSE AND PVP

(75) Inventors: Stephen A. Livesey, Conroe; Anthony A. del Campo, Houston; Abhijit Nag; Ken B. Nichols, both of The Woodlands; Carmen Piunno, Houston; David P. Ross, Katy, all of TX (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

(21) Appl. No.: 09/114,433

(22) Filed: Jul. 13, 1998

Related U.S. Application Data

(62) Division of application No. 08/752,740, filed on Nov. 14, 1996, now Pat. No. 5,780,295, which is a continuation of application No. 08/291,340, filed on Aug. 17, 1994, now abandoned, which is a division of application No. 08/018,357, filed on Feb. 16, 1996, now Pat. No. 5,364,756, which is a continuation of application No. 07/709,504, filed on Jun. 3, 1991, now abandoned, which is a continuation-in-part of application No. 07/581,584, filed on Sep. 12, 1990, now abandoned.

(51) Int. Cl.$^7$ .................................................. A01N 1/02

(52) U.S. Cl. ............................................. 435/1.3; 435/1.1

(58) Field of Search ........................................ 435/1.3, 1.1

(56) References Cited

U.S. PATENT DOCUMENTS

| | | | |
|---|---|---|---|
| 3,228,838 | 1/1966 | Rinfret | 167/74 |
| 4,329,787 | 5/1982 | Newton . | |
| 4,559,298 | 12/1985 | Fahy | 435/1 |
| 4,567,847 | 2/1986 | Linner | 118/50.1 |
| 4,688,387 | 8/1987 | Conaway | 435/1 |
| 4,707,998 | 11/1987 | Linner et al. | 62/349 |
| 4,807,442 | 2/1989 | Linner et al. | 62/55.5 |
| 4,865,871 | 9/1989 | Livesey et al. | 427/4 |
| 4,874,690 | 10/1989 | Goodrich, Jr. . | |
| 4,964,280 | 10/1990 | Piunno et al. | 62/78 |
| 4,980,277 | 12/1990 | Junnilla | 435/240.1 |
| 5,024,830 | 6/1991 | Linner et al. | 435/1 |
| 5,045,446 | 9/1991 | Goodrich, Jr. . | |
| 5,153,004 | 10/1992 | Goodrich, Jr. . | |
| 5,171,661 | 12/1992 | Goodrich, Jr. | 435/1 |
| 5,178,884 | 1/1993 | Goodrich . | |

FOREIGN PATENT DOCUMENTS

| | | |
|---|---|---|
| 614532 | 11/1979 | (CH) . |
| 0 267 026 | 11/1988 | (EP) . |
| 1522286 | 3/1968 | (FR) . |
| 2104349 | 3/1972 | (FR) . |
| 351132 | 6/1931 | (GB) . |
| 1482785 | 8/1977 | (GB) . |
| WO 91/18504 | 12/1991 | (WO) . |

OTHER PUBLICATIONS

Meryman, H.T., "Absence of Unfrozen Freezable Water in Rapidly Frozen Red Cells," 7 Cryobiology, pp. 252–255 (1971).

Terracio, L. and Schwabe, K.G., "Freezing and Drying of Biological Tissues for Electron Microscopy," 29 Journal of Histochemistry and Cytochemistry, pp. 1021–1028 (1981).

Coulter, H.D. and Terracio, L., "Preparation of Biological Tissue for Electron Microscopy by Freeze–Drying," 187 Anatomical Record, pp. 477–493 (1977).

Escaig, Jacques, "New Instruments Which Facilitate Rapid Freezing at 83K and 6K," Journal of Microscopy, Jun. 1982, pp. 221–22.

Boyne, Alan F., "A Gentle, Bounce–Free Assembly for Quick–Freezing Tissues for Electron Microscopy: Application to Isolated Torpedine Ray Electrocyte Stacks," Journal of Neuroscience Methods, 1, pp. 353–364 (1979).

Coulder, H. David, "Freezing and Drying of Biological Tissues With a Toggle–Link Helium Freezer and an Improved Freeze–Drying Apparatus: Application to Neuropeptide Immunocytochemistry," Journal of Electron Microscopy Technique, 4, pp. 315–328 (1986).

Reichert, Jung, "Cryovacublock"—Instruction Manual (No Date Provided).

Escaig, Jacques, "Control of Different Parameters for Optimal Freezing Conditions," Science of Biological Specimen Preparation, pp. 117–122 (No Date Provided).

Handley, Dean A., Alexander, Jack T., and Chien, Shu, "The Design and Use of a Simple Device for Rapid Quench–Freezing of Biological Samples," Journal of Microscopy, Mar. 1981, pp. 273–282, Polaron Instruments, Inc., "The Slammer," (Brochure).

Med–Vac, Inc., "Cryopress" (Brochure) (No Date Provided).

Reichert–Jung, "Cryofrace 190 Cryoblock" (Brochure) (No Date Provided).

(List continued on next page.)

Primary Examiner—Sandra E. Saucier
(74) Attorney, Agent, or Firm—Howrey, Simon, Arnold & White LLP; Stephen H. Cagle; Carter J. White

(57) ABSTRACT

This invention relates to methods, apparatus and solutions for cryopreserving microscopic biological materials for biologically extended periods of time. The method comprises treating a suspension of biological material, in an appropriate buffer, with a cryoprotectant or combination of cryoprotectants which raises the glass transition temperature range of the sample. One or more dry protectants may be added to the cryosolution. The cryosolution is then nebulized and rapidly cooled with novel apparatus, dried by molecular distillation, stored and then rehydrated in a buffer prior to its use. The solutions comprise novel mixtures of cryoprotectants.

1 Claim, 3 Drawing Sheets

OTHER PUBLICATIONS

Quick Freezing Devices, "Quick Freezing by Bounce–Free Delivery" (Brochure) (No Date Provided).

Moor, H., Bellin, G., Sandri, C. and Akert, K., "The Influence of High Pressure Freezing on Mamalian Nerve Tissue," Cell and Tissue Research, pp. 201–216 (1980).

Lejeune et al., Ann Pharm. Fr., 44(6), p. 461–466 (1986).

Hayakawa, K., Hakkokogaku Kaishi, 63(1), p. 17–22 (1985).

Roinel, N., J. Electron Microsc. Tech., 9(1), p. 45–46 May 1988.

Mayer, "New method for vitrifying water and other liquids by rapid cooling of their aerosols" Jul. 15, 1985 J. Appl. Phys. 58(2) Jul. 1985 pp. 663–667.

FIG.1

```
PREPARATION
OF
CRYOSOLUTION
     │
     ▼
 NEBULIZATION
     │
     ▼
   COOLING
     AND
  COLLECTION
     │
     ▼
    DRYING
     │
     ▼
  REHYDRATION
```

CRYOPROTECTIVE SOLUTIONS COMPRISING DMSO, PG, 2,3-BUTANEDIOL, RAFFINOSE AND PVP

This is a divisional of application Ser. No. 08/752,740 filed Nov. 14, 1996, now U.S. Pat. No. 5,780,295 which is a continuation of application Ser. No. 08/291,340 filed Aug. 17, 1994, now abandoned which is a divisional of application Ser. No. 08/018,357, filed: Feb. 16, 1993, now U.S. Pat. No. 5,364,756, which is a continuation of application Ser. No. 07/709,504, filed on Jun. 3, 1991, now abandoned, which is a continuation-in-part of application Ser. No. 07/581,584 filed on Sep. 12, 1990 now abandoned.

This invention was made with Government Support under Grant N00014-90-C-0193 awarded by the Department of the Navy. The Government has certain rights in the invention.

BACKGROUND OF THE INVENTION

1. Field of the Invention

This invention relates to methods and apparatus for preparing biological suspensions for long term preservation in the dry state for later use. These methods avoid deleterious modifications of the biological ultrastructure during the preservation process. More particularly, the present invention relates to the preservation of microscopic biological materials which are found or placed in a suspension prior to treatment.

In its preferred form, the method of this invention includes the steps of preparing a cryosolution by treating a biological material with a protectant or combination of protectants, cooling, storing under temperature conditions which preclude devitrification or recrystallization, and drying under controlled temperature, vacuum and condenser conditions. The biological material can be rehydrated prior to use if desired.

2. Description of the Related Art

The desire to preserve biological materials at ambient conditions for future use has existed for a long time in the scientific community. For example, the dry preservation of erythrocytes has been attempted by several groups over the last 30 to 40 years. The ability to dry the erythrocytes and reconstitute them at a later date at ambient conditions would have far reaching benefits during times of disaster, wars, and in remote locations. It would be a significant advancement in the art to be able to store dried, powdered erythrocytes in a sterile container such that they could be reconstituted by simply adding an appropriate buffered solution prior to use.

Similarly, freeze drying of cultured mammalian cells has been attempted without success. With the advent of biotechnology and the identification of functionally important cells, e.g., hepatocytes and pancreatic islets, a method of prolonged storage under ambient conditions would be invaluable.

Many complex macromolecules, either antibodies or recombinant proteins which are to be used therapeutically, show reduced activity following freezing or freeze drying. The development of methods to enable prolonged ambient storage without significant loss of activity is an important component in their ultimate therapeutic effectiveness.

Further, the necessity to control or abate viral infections has been a major medical concern for decades. Basically, the eradication and/or control of viral infections involves the production of a variety of different and highly potent vaccines.

Quantitative and qualitative production of pure and potent viral antigens or immunogens is difficult as well as expensive. This is usually due to the fact that many viruses replicate very slowly, if at all, in controlled cell culture environments. If the virus of choice seldom replicates in the test tube, then the production of the specific viral particle becomes less favorable and effective, as well as more expensive. Therefore, it is essential that, once vaccine material is produced, its biological activity be preserved for an extended period of time.

One feature common to all these examples is that the initial configuration of the sample is a microscopic biological material in the form of a suspension or emulsion. Once an effective suspension has been produced, preserving and storing this material is of utmost importance.

The field of cryopreservation and dry stabilization is rapidly developing and advancing. Incorporated herein by reference is U.S. Pat. No. 4,865,871, issued Sep. 12, 1989 which describes an apparatus and method for the cryopreservation of a biological tissue sample. The method comprises treating a biological tissue sample with a cryoprotectant which raises the glass transition temperature range of the sample, vitrifying the tissue sample under cryogenic temperature conditions at a specific rate to preclude the formation of significant resolvable ice crystals, equilibrating the depressurized, vitrified tissue in a sample holder and then dehydrating the tissue sample by molecular distillation by the addition of energy until substantially no vaporized water can be detected in the atmosphere surrounding the tissue sample.

The first critical processing step in cryopreservation must be performed in such a way as to satisfy two essential criteria. First, the biological material must not undergo irreversible damage due to the multiplicity of changes which occur within a sample during cooling. These changes include mechanical damage due to ice formation, cell-to-cell fusion due to the decrease in the solute volume available, and changes in acidity (pH) and salt or solute concentrations due to the segregation of solute and water. Second, the condition of the sample following cooling must be compatible with subsequent drying and reconstitution. This includes such parameters as sample size, ice forms created, and the nature and final concentration of additives or excipients.

In satisfying these two criteria, the cryopreservation process represents a balance between the use of cryoprotective agents (CPA's) to minimize changes during freezing by chemically increasing the volume of the ice free zone for a given cooling rate, and the cooling rate itself. Several potential combinations are possible, some of which are summarized in the following table:

| Cooling Mode | Approximate Cooling Rate | Final CPA Concentration |
| --- | --- | --- |
| Ultra Rapid | 300,000° C./sec. | Zero |
| Rapid | 50,000–100,000° C./sec. | Low |
| Intermediate | 500–2,500° C./sec. | Intermediate |
| Slow | 1–20° C./min. | High |

Inherent in most processes for cryopreparation and freezing of biological materials is the concomitant artifact creation, sample shrinkage and resultant damage to and modification of sample characteristics. These sample characteristic modifications, whether in the form of artifacts or the like, must be controlled and minimized. The acceptable limits for sample modification are defined by the anticipated end use of the cryoprepared material. For example, slow rate cooling results in extremely high final concentrations of CPA to which the sample is exposed. This results in potential deleterious effects at each step of the process. These include toxicity during cooling, incompatibility during drying and severe osmotic stresses during rehydration.

One of the problems which has been encountered in cryopreservation has been the lack of an effective and efficient apparatus and method for rapidly cooling suspensions of biological materials. Some prior art processes have utilized air guns or air brushes to generate microdroplets which are then cooled. However, these devices cause shear stresses which damage the cellular material. Additionally, in the prior art processes, the microdroplets were sprayed directly into a liquid cryogen. This posed problems in collection of the frozen microdroplets and also had the potential for contaminating the sample. Accordingly, there has existed in the art a need for a method and apparatus for the cryopreparation of a suspension of biological materials which was practical, cost effective and sterile.

Various processes have been utilized in the past for drying frozen biological samples. These include freeze drying and molecular distillation drying. Examples of apparatus and methods used in molecular distillation drying are disclosed in U.S. Pat. Nos. 4,510,169, 4,567,847, 4,676,070, 4,799,361, 4,865,871 and 4,964,280.

Thus, it would be an important advancement in the art to provide methods and apparatus of cryopreparing and dry stabilizing biological samples without overt disruption or destruction of the morphological characteristics of the ultrastructure of the sample. Such methods and apparatus should provide for the cryostabilization of microscopic, biological samples by dehydrating the samples, in which the water molecules are maintained in a predetermined optimal ice phase, without creating unnecessary artifacts and resultant undesired ultrastructural and morphological damage while the water is being removed.

BRIEF DESCRIPTION OF THE DRAWINGS

FIG. 1 is a schematic flow diagram of the method of this invention.

SUMMARY OF THE INVENTION

Figure 2:
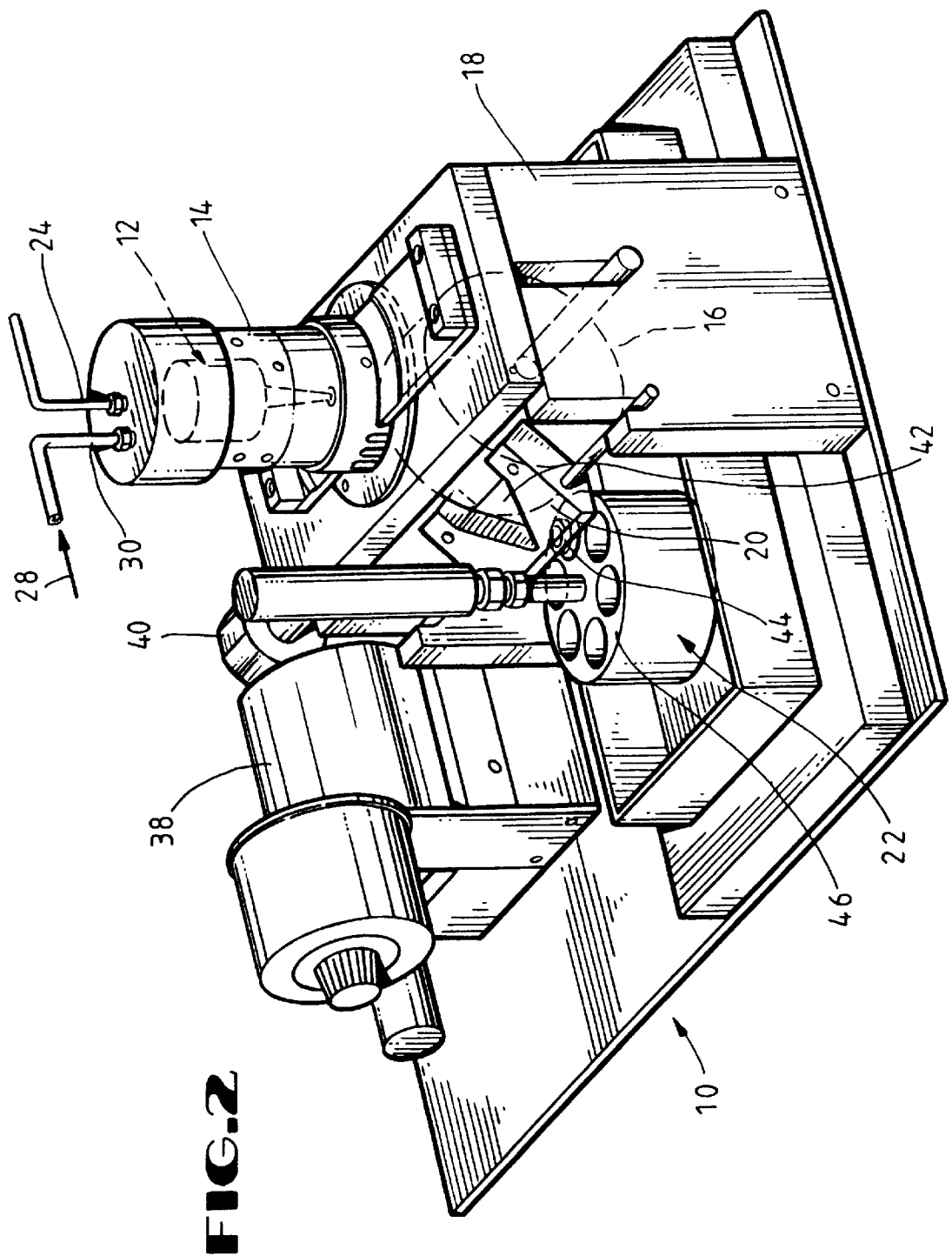
FIG. 2 is a perspective view of a rapid cryofixation device forming a part of this invention.

The present invention relates to a method and apparatus for cryopreserving and drying microscopic biological materials which are generally prepared in a suspension. As used in this application, suspensions also include emulsions. The method of this invention includes the cryopreparation and dry stabilization of the biological materials.

In the preferred embodiment, the cryopreparation is achieved by first preparing a cryosolution of the biological material which includes an appropriate buffer, one or more cryoprotectants and/or dry protectants, and a suspension of the biological material. The cryosolution is then cooled in such a manner to functionally result in the formation of amorphous phase ice, cubic phase ice and hexagonal phase ice in the cryosolution without damaging the structure or morphology of the biological material. The cryosolution is then dried to remove the various ice phases to a final product with residual water content less than about 5%, preferably less than about 3%.

The sample is pretreated with protective agents, i.e. cryoprotectants and dry stabilizers, and subjected to cooling rates and final temperatures that minimize ice crystal formation. It should be understood that the process of this invention is adaptable to whatever specific end use is contemplated. For example, in certain situations an absolute minimum amount of ultrastructural damage may be tolerated while in other applications the end use may not be as sensitive to cell morphology. By the proper selection of cryoprotective agents and the use of preselected drying parameters, almost any biological sample in suspension can be cryoprepared for a suitable desired end use.

After functionally effective amounts of cryoprotectants and/or dry stabilizers have been added to the sample, the sample is cooled to a temperature at which chemical activity is essentially arrested. The cooling is completed in a fashion such that the crystalline structure of the liquid molecules within the biological material cause minimal levels of damage.

Cooling of the solution is achieved by nebulizing the solution to form discrete droplets, said droplets being less than about 200 $\mu$m in diameter. The microdroplets are then sprayed onto a rotating cryogenic surface which is internally cooled by a cryogenic fluid to a temperature of less than about $-160°$ C. The frozen microdroplets are mechanically removed from the rotating cylinder by a collector, also cooled by internal cryogen, and are placed in a sample collection device for subsequent drying.

Drying of the frozen microdroplets is accomplished by use of a conventional freeze dryer or a molecular distillation dryer which is known in the art and is discussed further below. Where conventional freeze drying is used, the unique aspect of the method relates to the microdroplet configuration and the lack of damage during microdroplet formation using low frequency ultrasound. As freeze drying is currently performed at temperatures above $-70°$ C., water within the sample will exist either as hexagonal ice or in combination with the cryoprotectant in the ice free zone of the sample. The efficiency of drying will be greatly augmented by the microdroplet configuration of the sample. Molecular distillation drying is performed under conditions of temperature and pressure that result in the removal of crystalline fluids without substantial ultrastructural damage.

In the context of molecular distillation drying, the drying process associated with the process of this invention is referred to as transitional, phasic drying. This means that water, in the form of ice crystals, is removed from the cooled samples during the transition temperature from one ice phase to another, e.g., from cubic to hexagonal.

Also, in the preferred method of this invention, the dried biological solution is placed in a biologically inert container in a dry inert gas atmosphere or at low pressure. In this fashion, the biological materials can be cryoprepared, dry stabilized and preserved for biologically extended periods of time.

The present invention can be used to preserve many different types of biological materials. It is anticipated that the method can be used to preserve materials such as red blood cells, mammalian cultured cells, platelets, leukocytes, Factor VIII, sperm, pancreatic islets, marrow cells, viruses and vaccines. Suitable materials can be either molecular, viral, bacterial, cellular, or subcellular.

Thus, it is an objective of this invention to control and minimize undesirable artifact formations while preserving and storing biological samples. It is essential to emphasize that throughout preservation and storage of the samples, the activity and integrity of the samples should be maintained.

The method of this invention represents a cryostabilization breakthrough that permits preserving and storing dried, microscopic biological materials prepared as a suspension. This invention is cost effective, safe and the samples that are stored maintain their biological activity even after extended periods of storage. The specific desired extended time period will depend on the biologic material being preserved and the intended end use. Inexpensive and effective preservation and storage of potent biological materials is a necessity for the field of biotechnology to advance.

It has recently been postulated and confirmed that there is a direct correlation between the temperature of a biological material sample and the crystalline configuration of the fluid molecules in the sample. The understanding of this interrelationship has facilitated the development of the process of this invention in which the control of the sample temperature results in the control of crystalline structure and thus the control of ultrastructural damage. Importantly, the crystalline configuration of the fluid molecules has a direct bearing on the damage done to sample morphology and function.

DESCRIPTION OF THE PREFERRED EMBODIMENTS

The present invention provides a method and apparatus for preserving microscopic biological materials through the steps of cryopreparation and dry stabilization.

The method of the present invention can best be understood by reference to FIG. 1 which schematically illustrates the steps involved in the method of the present invention.

In the preferred embodiment, the microscopic biological material to be preserved is first formulated into a cryosolution. The cryosolution generally contains a suspension of the biological material, an appropriate buffer and one or more cryoprotectants and/or dry stabilizers. The type and amount of buffer and protectant can be varied and is determined by the particular material being preserved and its intended end use. Under certain applications, no protectant need be used. Under other applications, various concentrations and combinations of protectants and dry stabilizers can be used as discussed further below.

After the cryosolution has been prepared, it must be nebulized before it can be cooled. In the preferred embodiment, a low wattage, low frequency, ultrasonic nebulizer is used to create the microdroplets.

In the preferred embodiment, the nebulized cryosolution is directed to a cryogenic surface for rapid cooling. The nebulized cryosolution should be directed to the surface under conditions such that it does not undergo any substantial, slow precooling prior to the rapid cooling event.

In the preferred embodiment, a continuously replenished cryogenic surface is utilized to rapidly cool the nebulized cryosolution. It comprises a rotating metal cylinder which is internally cooled with a liquid cryogen.

The frozen cryosolution is removed from the cryogenic surface and placed in a suitable collection device such that it can be transferred to a suitable drying apparatus. It is important that the frozen cryosolution remain at cryogenic temperatures during all steps including transportation from the freezing device to the dryer. In addition, it is important that the cryosolution at no time comes into contact with liquid cryogen which has been introduced into the device to provide cooling. The frozen cryosolution in the collection device can either be taken directly to a dryer or stored at cryogenic temperatures.

In the preferred embodiment, drying is achieved either by conventional freeze drying or by using a molecular distillation dryer. Suitable molecular distillation dryers can be obtained from LifeCell Corporation in The Woodlands, Tex. and are disclosed in U.S. Pat. Nos. 4,567,847 and 4,799,361 which are incorporated herein by reference.

Figure 3:
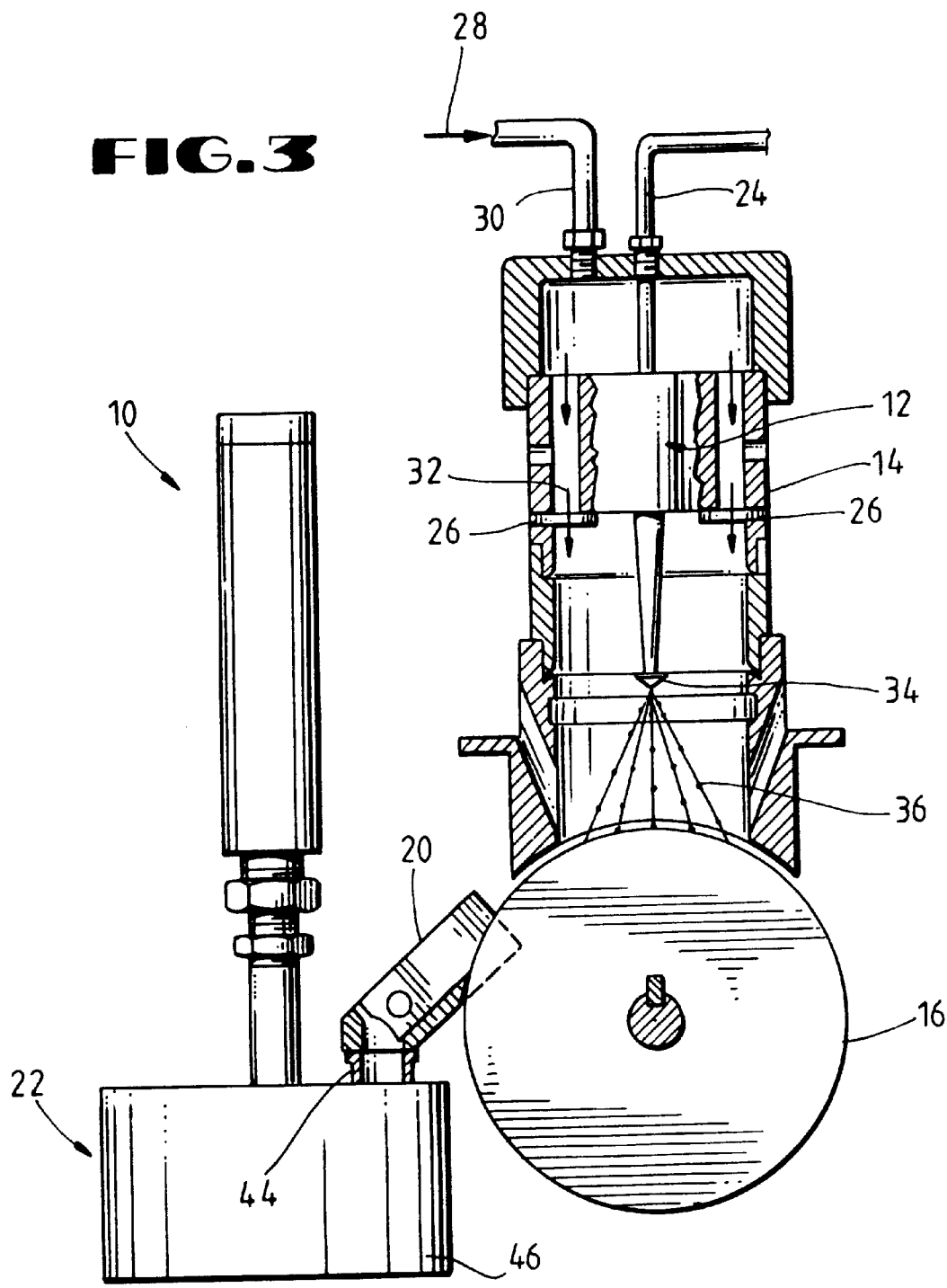
FIG. 3 is a cross-sectional view of a portion of the apparatus illustrated in FIG. 2 generally taken along lines 3—3.

The preferred cooling apparatus to be utilized in the practice of the present invention is a novel cryofixation device illustrated in FIGS. 2 and 3.

Referring now to FIGS. 2 and 3, the rapid cryofixation device is generally referred to at 10. It comprises a nebulizer 12 positioned within a nebulizer column 14. A cryogenic surface 16 is positioned at the outlet of nebulizer column 14 and is contained within a housing 18. A collector 20 is positioned adjacent cryogenic surface 16 to remove the frozen cryosolution and position it within a sample holder 22. Sample holder 22 can be used to transport the frozen cryosolution to a molecular distillation dryer where it is further processed or to a storage area.

Nebulizer 12 is a low wattage, low frequency, ultrasonic nebulization device such as an ultrasonic atomizing nozzle available from Sonotek. The nebulizer was modified with respect to cryosolution delivery to minimize contact of the cryosolution with the nebulizer components. This was achieved by bypassing the normal fluid conduit and delivering the cryosolution only to the tip of the nebulizer via a sterilized, disposable conduit 24. In this way, exposure of the cryosolution to heating and ultrasonics was minimized. This configuration is also important to maintaining sterility of the cryosolution during processing. Sterility was one of the problems encountered in prior art processes which used air guns or sprays. Conduit 24 is connected to a suitable container (not shown) which holds the cryosolution.

This particular nebulizer can form microdroplets with diameters on the order of about 25 $\mu$m to about 250 $\mu$m. Diameters on the order of 25 to 200 $\mu$m are appropriate for rapid cooling. Microdroplet diameters on the order of 25 to 100 $\mu$m are preferred in order to achieve maximum cooling rates and short drying times. The nebulizer can be adjusted to achieve cryosolution flow rates of 5–10 ml. per minute without significant damage to the biological material.

Nebulizer 12 is mounted within nebulizer column 14 by suitable brackets 26. A dry gas 28 at room temperature is introduced into the top of column 14 through tubing 30. Nebulizer 12 is mounted in such a manner that gas 28 can flow past nebulizer 12 with laminar flow as indicated by arrows 32. The flow of inert gas 28 ensures that the nebulized sample does not undergo a slow precooling process prior to rapid cooling on cryogenic surface 16. Many different types of gases may be utilized such as nitrogen, helium, oxygen and argon. The flow rate of the gas should be adjusted so as to prevent slow precooling but should not be so high as to cause turbulent flow or significant warming of the cryogenic surface.

The cryosolution containing the microscopic biological sample is discharged from nozzle 34 of nebulizer 12 as microdroplets 36 which quickly encounter cryogenic surface 16.

In the preferred embodiment, cryogenic surface 16 comprises a hollow cylinder with high thermal conductivity presenting a rotating mirror finished metal surface. The thermal capacity of this surface together with internal cryogen is such that the nebulized sample can be rapidly cooled without contacting the liquid cryogen. A suitable drive motor 38 and gear mechanism 40 are used to rotate cryogenic surface 16.

The rate of rotation is dependent upon the size of the cryogenic surface and the flow rate of the cryosolution. In the preferred embodiment, the cryogenic surface has a diameter of about 4 inches, a width of about 2 inches and a length of about 12 inches.

The cylinder of cryogenic surface 16 is internally cooled with a liquid cryogen which is introduced into the cylinder through suitable connections. This allows the cryosolution to be cooled without contact with the cryogen which could cause problems with sterility. Additionally, by using a high thermally conductive metal as the conduit for heat flow between the sample and the liquid cryogen, vapor formation due to heating of the liquid cryogen which usually surrounds and insulates the sample from the thermal sink is avoided. This allows the achievement of much higher cooling rates.

The cylinder of cryogenic surface 16 can be formed of materials such that it is a permanent portion of the cryofixation device or can be designed with a disposable configuration. Suitable materials include copper, aluminum and chromium or diamond coated aluminum.

Microdroplets 36 which are frozen on cryogenic surface 16 are removed by collector 20 which is formed from an autoclavable material such as polyethylene terephthalate. Collector 20 includes a blade 42 for removing the frozen microdroplets from the cryogenic surface 16. They are then directed into a suitable sample holder 22. In one preferred embodiment, sample holder 22 comprises a sample vial 44 and a vial holder 46. In the illustrated embodiment, vial holder 46 is designed to hold six sample vials. The sample holder is designed such that it can be removed from cryofixation device 10 and placed within a molecular distillation dryer for drying of the cryosolution.

In another preferred embodiment, sample holder 22 comprises a collection bag held in a precooled transfer carrier similar to vial holder 46. The bag is fabricated from a suitable material such as polytetrafluoroethylene (PTFE) having a 15 micron pore size. This allows the sample to be contained within the bag while allowing water vapor to escape during drying. Following collection, the bag is sealed to contain the sample through subsequent processing steps.

In the practice of this invention, it is a fundamental prerequisite that suitable desired biological samples be obtained. Virus or vaccine samples, antibodies and recombinant proteins are commercially available from a variety of sources. The particular type of virus or vaccine sample, antibody or recombinant protein is not limiting on the method of this invention. However, the cryopreservation of the biological sample is enhanced if the sample to be processed is fresh.

Human erythrocytes can be obtained fresh from donors and collected in appropriate anticoagulant containers and subjected to separation and washing procedures. Alternatively, erythrocytes can be processed from standard blood bank supplies if they are used within six days of collection.

The cryopreparation of the biological sample takes place preferably immediately after it is received. Biological materials generally undergo significant deterioration during freezing and thawing or following freeze drying by conventional means. Accordingly, these steps should be avoided prior to processing by the method described in this application.

The initial steps of cryopreserving the biological samples includes preparing a cryosolution prior to the cooling step. The cryosolution comprises a biological suspension, an appropriate buffer and one or more cryoprotectants and/or dry protectants.

Microscopic biological samples are most often obtained as a suspension. The exact ingredients of each available suspension is not considered to be a component of this invention. The detailed composition of each suspension will vary from source to source and the specific ingredients may often involve proprietary information. However, in general, microscopic biological suspensions include a mixture of a percentage of biological material in water, phosphate buffered saline or another compatible solution. If the solution composition is not compatible with the cryopreservation process, the undesired components may be eliminated by concentrating the biological suspension. The biological sample may then be resuspended in a compatible solution.

In addition to the biological suspension, the cryosolution generally contains an appropriate buffer. This may involve one of many different organic buffers which are known to those skilled in this art. The inventors prefer to use an organic buffer selected from the group consisting of: Tris (2-Amino-2-(hydroxymethyl)-1,3-propanediol); MES (2-[N-Morpholino] ethanesulfonic acid); Ammediol (2-amino-2 methyl-1,3-propanediol); MOPS (3-[N-Morpholino] propanesulfonic acid); and PIPES (Piperazine-N-N'-bis [2-ethanesulfonic acid] and 1,4-Piperazine-diethanesulfonic acid).

Alternatively, a low salt or physiological buffer may be more appropriate in certain applications. Low salt buffers include mixtures currently used in blood storage such as (1) LISS—8 gms glycine, 20 mls of 0.15M phosphate buffer pH 6.7–8.4 and 1.8 gm sodium chloride made up to 1000 mls pH 6.7; (2) LISP—16 gms glycine, 20 mls of 0.15M phosphate buffer pH 6.7–8.4, 1.8 gm sodium chloride, 5.0 gms glucose, 0.06 gm calcium chloride and 0.1 gms adenine made up to 1000 ml pH 6.7; (3) Adsol—0.9% NaCl, 0.75% mannitol, 2.2% dextrose, and 0.027% adenine; (4) RBC Buffer—0.875% dextrose 0.9% NaCl, 0.214% mannitol, 0.008% adenine, 0.255% sodium citrate, 0.029% citric acid, and 0.022% monobasic sodium phosphate; or modifications thereof such as (5) Buffer A—16 mM phosphate buffer, pH 7.4, 5 mM KCl, 4 g/dl BSA and lactose 6.9 g/lit, and (6) Buffer B—16 mM phosphate buffer, pH 7.4, 5 mM KCl and lactose 15 g/lit. Physiological buffers include various phosphate buffered saline solutions. Additional buffers of importance are those containing magnesium as a component.

The cryosolution also generally contains a cryoprotectant. Cryoprotectants raise the glass transition temperature range of the sample thereby stabilizing the sample in the frozen state. By raising this range, the sample can be dried at a faster rate. The cryoprotectant also permits decreased ice formation for a given cooling rate allowing vitrification of larger samples. With current methods of ultrarapid cooling in the absence of cryoprotectants, vitrification of the sample is only achieved to a depth of a few microns. Cubic and hexagonal ice are then encountered. By appropriately selecting the cryoprotectant and the cooling method, apparent vitrification to a depth of several millimeters can be achieved.

Various cryoprotectants can be used in the present invention. These include: dimethyl sulfoxide (DMSO), dextran, sucrose, 1,2 propanediol, glycerol, sorbitol, fructose, trehalose, raffinose, hydroxyethyl starch, propylene glycol, 2-3 butane diol, polyvinylpyrrolidone (PVP), proline (or other protein stabilizers) human serum albumin and combinations thereof. Suitable cryoprotectants structure water which reduces the freezing point and/or reduces the rate of cooling necessary to achieve the vitreous phase. They also raise the glass transition temperature range of the vitreous state.

The cryosolution may also include exposing the biological suspension to one or more dry protectant compounds. Dry protectants, by definition, stabilize samples in the dry state. Some cryoprotectants also act as drying protectants. Some compounds possess variable amounts of each activity, e.g., trehalose is predominantly a dry protectant and a weaker cryoprotectant, whereas sucrose is predominantly a cryoprotectant and a weaker dry protectant. For example, trehalose and polyhydroxyl carbohydrates bind to and stabilize macromolecules such as proteins and nucleic acids in a virus or vaccine sample when dried, thereby protecting the integrity of the sample. Various dry protectants can be used in the present invention: sucrose, raffinose, trehalose, zinc, proline (or other protein stabilizers), myristic acid (a known thermostabilizer of vaccines), spermine (a polyanionic compound) and combinations thereof.

Cryoprotectants, alone or in combination with other cryoprotectants or with additional components (for example, dry protectants) have also been found to be effective: proline plus sorbitol, trehalose plus zinc chloride, sorbitol plus myristic acid, sorbitol plus trehalose, human serum albumin plus trehalose, sucrose plus raffinose, and human serum albumin plus sorbitol.

The cryoprotectants can be added to the biological samples for a period of a few minutes to a few hours before they are rapidly cooled. In general, cryopreservation is performed as a continuous sequence of events.

The inventors have been involved in the development of cryofixation and ultralow temperature molecular distillation drying as a method for preparing biological samples for electron microscopic analysis. To validate this approach, they investigated the relationship between the drying characteristics and ice phases present within frozen samples.

Sample preparation for electron microscopy by purely physical or dry processing techniques has theoretical appeal, especially when the ultimate aim is the analysis of both ultrastructure and biochemistry. Since the earliest days of electron microscopy, several attempts have been made to refine and develop freezing and vacuum drying or the freeze-drying (FD) process for cell and tissue samples.

Despite the conceptual advantages and the progress made, freeze-drying for electron microscopy has yet to achieve the status of a routine, broadly applicable technique. Several reasons account for this. First, the ultrastructural preservation is often inferior when compared to conventional chemical, or wet processing techniques or hybrid techniques such as freeze substitution. Second, there are numerous practical problems with sample manipulation, temperature control, vacuum parameters, and end processing protocols. Third, and perhaps most fundamentally, is a belief that drying at temperatures below −123° C. is either impossible or impractical. As a result of these practical and theoretical obstacles, only sporadic investigation of low temperature freeze-drying has been reported.

The basis of this theoretical barrier comes from application of the kinetic gas theory and the predicted sublimation rates as expressed by the Knudsen equation:

$$Js = NPs\left(\frac{M}{2\pi QT}\right)^{0.5}$$

where Js=sublimation rate
N=coefficient of evaporation
Ps=saturation vapor pressure
Q=universal gas constant
T=absolute temperature of the sample
M=molecular weight of water.

For theoretically ideal drying conditions, this equation states that the sublimation rate is directly proportional to the saturation vapor pressure of water within the sample and inversely proportional to the absolute temperature of the sample. Although the temperature of the sample is clearly definable, saturation vapor pressure is a more complex parameter.

Prior applications of this equation have used saturation vapor pressures which were theoretically determined. These theoretical vapor pressures, however, include the latent heat of fusion, and hence, are applicable only to hexagonal ice. Calculations based on these theoretical values have led to conclusions such as "at 150K it would take 3.5 years until an ice layer of 1 mm thickness is completely removed by freeze drying. It is therefore unrealistic to attempt freeze drying at temperatures below 170K."

Several phases of ice other than hexagonal, however, can coexist within a sample depending upon the mode of cooling. These different phases can be achieved by several methods including; vapor condensation, hyperbaric application and ultrarapid quench cooling.

The major phases of ice now recognized are amorphous, cubic, and hexagonal. These ice phases exhibit different stabilities, which would suggest that the saturation vapor pressures would also be different. It has been determined that for vapor condensed water at temperatures where both phases can coexist, the saturation vapor pressure of amorphous ice is one to two logs higher than that of cubic ice.

Application of these experimentally determined saturation vapor pressures in the Knudsen equation reduces the drying time at 150K from 3.5 years to 0.035 years, or 12.7 days, for 1 mm of amorphous ice. Because quench cooling techniques of biological samples achieve approximately 5 μm of this phase, the drying time of this component, based solely on the Knudsen equation, would be of the order of 1.5 hours. Hence, in terms of practical drying times, the theoretical barrier to drying at ultralow temperatures can be overcome.

Drying, however, is not a static, but a rate-dependent process. In addition to saturation vapor pressure of the different ice phases, one must also account for the rate of transition from one phase to another with increasing temperature. For electron microscopy sample preparation, drying should ideally occur without any such transition or devitrification. Information as to the rate of these transitions is limited. It has been found that the amorphous to cubic transition occurred as an irreversible process strongly dependent upon temperature in the range of −160° C. to −130° C. and expressed by $$t=2.04\times10_{28}\times exp\ (-0.465T)$$

The cubic to hexagonal transition was less temperature-dependent, occurring in the range of −120° C. to −65° C., and expressed by $$t=2.58\times10_{12}\times exp\ (-0.126T)$$

Interestingly, when the sample temperature was increased at a rate of 5° C./minute, the amorphous to cubic transition occurred as a sudden event near −130° C.

Based upon the above data, the transition rate, as well as the saturation vapor pressure, determine the depth to which a particular ice phase can be dried at a specific temperature. For amorphous ice at −160° C., the transition time is 205 days. Based upon extrapolation of experimentally determined saturation vapor pressures and the Knudsen equation, this would allow drying of 26 microns. At −140° C., transition time is 28 minutes and would allow drying of 0.8 $\mu$m under ideal conditions. Below −160° C., i.e., prior to the onset of the transition, one could predict little, if any, translational kinetic energy of the water molecules and hence little, if any, drying.

Based upon these considerations, one can postulate the hypothesis of transitional drying, i.e., that for a sample containing multiple phases of ice, it is possible to dry each phase sequentially during its transition. The amount of each phase dried will obviously be dependent upon multiple parameters including efficiency of drying apparatus, rate of heating, and impedance of the dry shell.

Cryopreservation

Cryopreservation is the preservation of cell structure and metabolism against injury associated with freezing events either within or around the cell. Natural cryoprotection can result from adaptive metabolism of the organism, with changes in cellular structure, composition and metabolic balance giving an enhanced tolerance of freezing. In laboratory experiments when cell viability or ultrastructure are to be preserved following cooling, two methods are available. The first is to ultrarapidly cool the sample, resulting in the tissue fluids being vitrified, i.e., absence of ice crystals. The second is to incorporate chemical additives to confer a degree of cryoprotection. The chemicals range from naturally occurring cryoprotectants such as glycerol, proline, sugars, and alcohols to organic solvents such as dimethylsulfoxide (DMSO) to high molecular weight polymers such as polyvinylpyrrolidone (PVP), dextran and hydroxyethyl starch (HES).

Vitrification of cells and tissues is limited by the rate at which the sample can be cooled and the insulating properties of the tissue itself. Due to physical limitations, one can only achieve vitrification of a thin layer of tissues using state of the art techniques. This makes the idea of chemical additives for cryoprotection and manipulating the cooling rate very appealing in attempts to cool and store biological samples without causing structural and functional damage.

Injury to biological samples due to freezing is subject to fundamental physical and biological principles, some long known, but others only recently being understood. Serious investigations into the mechanisms of freezing injury in biological samples did not begin until the second quarter of this century. These early studies were dominated by the belief that physical damage by ice crystals was the principal cause of freeze injury. The effects of cell dehydration and a correlation between the concentration of extracellular solutes and cell death has been demonstrated. A "two factor" hypothesis for freezing injury proposed that cell injury was the result of either the concentration of solutes by extracellular ice or the formation of intracellular ice which caused mechanical injury.

The action of glycerol and other small polar compounds has been interpreted as penetrating and exerting colligative action within the cells. In the proportion that the colligative action of the penetrating compounds maintains water in the liquid state at temperatures below 0° C., an increased volume of cellular solution is maintained. This avoids an excessive concentration of toxic electrolytes in the nonfrozen cellular solution. A similar influence also takes place in the external solution. In this context, colligative action is referred to as action by an extraneous solute, in lowering the freezing point of the solution in contact with ice. If enough protective compound is present, the salt concentration does not rise to a critically damaging level until the temperature becomes so low that the damaging reactions are slow enough to be tolerated by the cells.

The nonpenetrating cryoprotectants vary in size from sucrose to large polymeric substances such as PVP, HES and dextran. It has been suggested that nonpenetrating substances act by some other means than that in the colligative mechanism described above. The role of larger molecules is believed to be dehydrative by osmotic action. When a large proportion of water is withdrawn from the cells by means of an osmotic differential, less free water is available for intracellular ice crystallization which is often identified as a lethal factor.

The cooling rate in the presence of cryoprotective compounds is a very important factor in freezing injury. Normally, slow cooling is better than elevated cooling rates since the latter promotes intracellular ice formation. This occurs because there is insufficient time for water to escape from the cells before the contained cell water freezes. With slow rate cooling, extracellular ice forms first, resulting in dehydration of the cell which, together with the presence of the cryoprotectant, prevents intracellular ice formation.

Penetrating compounds were thought to act by not allowing an excessive transport of water from the cells too early in the freezing process while nonpenetrating compounds have a dehydrative effect on cells along with a colligative effect of diluting the solution surrounding the cell. Neither of these descriptions, however, tells the whole story.

When cells were exposed to glycerol or DMSO for very short times, during which presumably little penetration would occur, they still exhibited cryoprotection. Red blood cells exposed to DMSO, glycerol or sucrose for 30 seconds to 2 hours at 0° C. demonstrated the same degree of cryoprotection.

Solutes such as HES and PVP are totally nonpenetrating, water withdrawing compounds of merely larger molecular weight than nonpenetrating sucrose. The larger molecular weight should render such compounds less osmotically and colligatively effective, when considered on a weight basis. Yet in concentrated solutions, the compounds' colligative action has been shown to be far greater than would be expected based on merely a linear relationship to concentration.

Cryoprotective properties result from a multiplicity of actions including: (1) coating of membranes by polymeric compounds so that they are not denatured by the increased salt concentration resulting from freezing, (2) alteration of membrane permeability characteristics so that they leak solutes reversibly to avoid excessive dehydration, (3) increasing viscosity and thus slowing the speed of transfer of water, (5) preventing denaturation of serum lipoproteins during low temperature freezing and drying, (6) diminished activity of several enzyme systems, and (7) membrane protein stabilization.

A source of damage to frozen tissue, other than freezing itself, is the osmotic and toxic effects of many of the cryoprotective agents. When used in mixtures, some cryoprotective compounds may counteract the toxicity of other cryoprotectants, as was demonstrated by the addition of polyethylene glycol (PEG) to a mixture of DMSO and glycerol. The inventors have developed a vitrification solution (VS) comprising a mixture of:

| | |
|---|---|
| DMSO | 0.5M |
| Propylene glycol | 0.5M |
| 2-3 butanediol | 0.25M |
| Proline | 1.0M |
| Raffinose | 2.5% (w/v) |
| PVP | 15% (w/v) (Ave. M.W. ≈ 40,000) |
| Dextran | 15% (w/v) (Ave. M.W. ≈ 40,000–70,000) |

The toxicity of the individual components of this solution were tested. In the above mixture, the toxic effects were lower than when the same concentration of any one component was used alone. This resulting solution is nontoxic to cell cultures and remains glass like and optically clear (i.e., no visible ice crystal is formed) when plunged into liquid nitrogen.

A modified vitrification solution ($VS_1$) has also been developed which comprises a mixture of:

| | |
|---|---|
| DMSO | 0.5M |
| Propylene glycol | 0.5M |
| 2-3 butanediol | 0.25M |
| Raffinose | 10% (w/v) |
| Trehalose | 6% (w/v) |
| Sucrose | 6% (w/v) |
| PVP | 12% (w/v) (Ave. M.W. ≈ 40,000) |
| Dextran | 12% (w/v) (Ave. M.W. ≈ 40,000–70,000) |

Another modified vitrification solution ($VS_2$) which has been developed comprises a mixture of:

| | |
|---|---|
| DMSO | 0.5M |
| Propylene glycol | 0.5M |
| 2-3 butanediol | 0.25M |
| Raffinose | 2.5% (w/v) |
| Sucrose | 12% (w/v) |
| PVP | 15% (w/v) (Ave. M.W. ≈ 40,000) |
| Dextran | 15% (w/v) (Ave. M.W. ≈ 40,000–70,000) |

In summary, the factors affecting the cryoprotective nature of compounds are (a) chemical nature, (b) relative lack of toxicity, (c) molecular size and penetrating ability, and (d) interaction with other compounds in the mixture.

The physicochemical effects of cryoprotectants are (a) depression of the equilibrium freezing point of substrate and cytoplasm on a colligative basis, (b) depression of homogeneous ice nucleation temperature, (c) reduced rate of ice crystal growth due to change in the viscosity and thermal diffusivity of the solution, and (d) dehydrative effects on cells by osmotic action.

Cooling Parameters

For purposes of cryopreparation of the biological suspensions of this invention, it is essential to note that a variety of cooling processes can be used. In a preferred embodiment of this invention, rapid cooling is considered essential to obtain the proper ice crystal blend. In the most preferred embodiment of this invention, a vitrification procedure is used which results in the formation of a substantial proportion of amorphous water in the biological sample. As will be disclosed hereinafter, regardless of the form of cooling that is used, it is believed that amorphous phase water, cubic ice crystals and hexagonal ice crystals are present in the final product. The method of cooling has a distinct bearing on the distribution of ice crystal types found in the cooled cryosolution.

Drying Parameters

The aim of controlled drying of a frozen biological sample by molecular distillation drying is to remove water from the sample without further mechanical or chemical damage occurring during the drying process. This involves avoiding, by use of appropriate drying conditions, two fundamental damaging events. The first is to remove water from ice crystalline phases without transition to larger more stable and more destructive crystals. The second is to remove water from solid but noncrystalline water or water-solute mixtures without melting or crystallization of these solid phases. This second component refers to water present in the amorphous condition, water together with solute in the eutectic or water together with a compound which binds and structures water and hence, prevents its crystallization during the freezing process. Hence, vitreous water can be of low energy and stability, as in ultrarapidly-cooled pure water, or high energy and stability, as that achieved with cryoprotective agents with intermediate rates of cooling.

Many of the features required of controlled drying to avoid the occurrence of these events are overlapping. The reason for this is that each form of water will have a particular energy state, whether in a crystal or bound to a cryoprotective compound, and it is this energy state, rather than its configuration, which determines the requirements for drying. Consider for example, (1) a sample of cubic ice achieved by cooling pure water at an intermediate cooling rate and (2) vitrified water achieved by mixing water with glycerol to 45% vol:vol and cooling at an intermediate rate. The first sample will be crystalline and the aim of drying is to remove water from this state without transition to hexagonal ice. The second sample is an amorphous solid and the aim of drying is to remove water from this phase without melting of the glass to a liquid with subsequent boiling. For cubic ice, the onset of its transition is −130° C. and the rate of transition is temperature dependent being very slow at −130° C. and very rapid at −90° C. For 45% glycerol-water, the glass transition temperature is −120° C. and represents the onset of melting. The melting process is very slow at −120° C. and is temperature dependent, becoming very rapid at −90° C.

Prior to the onset of the cubic to hexagonal transition or the glass transition of 45% glycerol-water, the saturation vapor pressure of water in these phases is extremely low and drying would occur at extremely slow rates. The aim of controlled drying, therefore, is to remove water from the cubic ice phase during its transition and in a time less than is required for any significant transition to hexagonal ice and from the 45% glycerol-water phase during its transition to a liquid but in less time than is required for any appreciable liquid to form.

This argument can be applied repetitively to all forms of water present whether it be crystalline in the form of cubic or hexagonal or noncrystalline as amorphous or bound to any molecule, be it cryoprotectant, protein, carbohydrate, or lipid. To simplify this concept, water in a frozen biological sample can be described as having a specific energy level E. In a frozen biological sample, there will be water forms of multiple definable energy levels:

$E_1\ E_2\ E_3$ - - - $E_n$

The mode of preparation, the nature of the sample, the use of cryoprotectants or other additives, and the cooling rate used will determine the relative proportions of these different water forms. Each energy level will determine the onset temperature of its transition or melting and the temperature dependence of the rate of the transition or melt.

Controlled drying processes must be able to remove each of these different states of water during the transition and in less time than is required to complete the transition. This mode of drying, therefore, requires that several conditions be met.

First, the sample must be loaded into the dryer without temperature elevation above its lowest transition temperature. If elevation of temperature does occur, this must be over a short period of time such that no appreciable transition occurs. Ideally, loading occurs under liquid nitrogen at −190° C., well below the lowest discernible transition of −160° C. for pure, ultrarapidly-cooled amorphous water. If, however, the sample is predominantly cubic ice or a mixture of water and cryoprotectants with a glass transition of the order of −100° C. to −130° C., a closed circuit refrigeration system may be sufficient to enable maintenance of the sample temperature below the onset of transition.

Once loaded, the sample must be exposed to vacuum and be in direct line of sight of the condenser surfaces. The criteria for these are again determined by the nature of the water phases present in the sample. The following objectives must be attained. The vacuum within the chamber during the drying of a particular phase must create a partial pressure of water at least equivalent to or less than the saturation vapor pressure of water in the phase to be removed. This saturation vapor pressure is dependent on the nature of the water phase and its temperature. Hence, for pure amorphous water in the transition range of −160° C. to −130° C., the approximate saturation vapor pressures are $6 \times 10^{-12}$ mbar (−160° C.) and $5 \times 10^{-7}$ mbar (−130° C.), respectively. As the transition times of amorphous to cubic ice in this same temperature range, −160° C. to −130° C., vary from $5 \times 10^5$ minutes to 5 minutes, drying will be very slow until temperatures of the order of −150° C. to −140° C. are reached requiring a vacuum of $5 \times 10^{-10}$ to $2 \times 10^{-8}$ mbar. This represents one extreme.

For cubic ice, little if any drying will occur below its onset of transition at −130° C. as its saturation vapor pressure will be of the order of one log lower than for amorphous water. In the transition range, −130° C. to −100° C., the saturation vapor pressure of cubic ice is approximately $5 \times 10^{-8}$ to $9 \times 10^{-5}$ mbar. The transition times of cubic to hexagonal are 700 minutes and 109 minutes respectively. The saturation vapor pressure, therefore, determines the vacuum requirements for drying and can be applied to all water phases present. It is important to note that the same vacuum criteria are not applicable to all phases, but rather are phase-dependent.

A second criteria of the vacuum is that the mean free path created be in excess of the distance between the sample and the condenser surface. Ideally, this should be a tenfold excess. The condenser surface must be a lower temperature than the onset transition temperature of the phase of water being removed from the sample so that the saturation vapor pressure of water condensed on this surface during drying is considerably lower than that of the water phase within the sample. Ideally, this should be three orders of magnitude lower. For a sample containing multiple water phases, the temperature of the condenser surface must remain below the onset of transition of the least stable ice phase remaining to be removed. Ideally, the condenser should also be in line of sight of the sample.

Once the sample has been loaded and exposed to vacuum and the condenser surfaces, the sample and sample holder must be heated so as to increase the mobility of water molecules and hence, cause their escape. This is the essential and critical component in the drying of a sample containing multiple phases or energy levels of water. The temperature of the sample must be accurately known. The control of temperature and the rate of sample heating must be accurately controlled. This is necessary to ensure that the drying of each phase of water in the sample is sequential.

Hence, for a sample containing multiple phases of water of energy level $E_1$, and $E_2$ - - - $E_n$, where $E_1$ is the least stable, then heating must occur at such a rate that $E_1$ is removed prior to its transition to $E_2$. $E_2$ prior to its transition to $E_3$ and so on. This requires nonequilibrium drying conditions and heating at a continuous rate or by holding at a constant temperature level such that sublimation occurs as determined by:

$$Js = NPs\left(\frac{M}{2\pi QT}\right)^{0.5}$$

where Js=sublimation rate in g cm$^{-1}$ sec$^{-1}$
N=coefficient of evaporation
Ps=saturation vapor pressure
M=molecular weight of water
Q=universal gas constant
T=absolute temperature of the sample.

This is consistent with the transition rate for the particular phase being removed. For example, the rate of the amorphous to cubic transition is given by:

$$E = 2.04 \times 10^{28} \times \exp(-0.465T)$$

Alternatively, if the transition window is $T_1$ to $T_2$, the sublimation rate and the transition rate will vary with temperature during this interval. The rate of heating during this window $T_1$ to $T_2$ must be such that sublimation occurs throughout the dimensions of the sample before transition at any particular temperature is completed.

In this way, the aim of controlled drying is achieved, i.e., the sequential removal of each phase of water under conditions appropriate to the properties of each phase without appreciable ice crystal growth, formation or melting of the particular phase. Once dry, the sample must be physically or mechanically isolated from water on the condenser surface or any other source and stored in a closed container either under vacuum or dry inert gas.

In a preferred embodiment, samples are cooled by an appropriate method such that ice crystal formation is below the degree that would cause damage to the sample. Once frozen, the sample is then stored below the transition temperature of the most unstable ice form. For amorphous ice, this is preferentially below −160° C. The sample is then loaded into a sample holder, precooled to −196° C. and transferred into a molecular distillation dryer. The dryer chamber is then closed and sealed for vacuum integrity. To avoid recrystallization, the hydrated sample must remain below the transition temperature of the most unstable ice form throughout all manipulations.

Once the sample is loaded, high vacuum ($10^{-8}$ to $10^{-6}$ mbar) is generated inside the chamber. The sample is placed considerably closer to the condenser surface (LN$_2$ cooled chamber walls) than the mean free path within the chamber. The condenser temperature must always be below that of the sample. For an amorphous sample, the condenser is preferentially −196° C.

The sample holder is then heated via a programmable heater microprocessor thermocouple loop. Heating programs are determined according to the nature of the sample. A typical program for a sample containing amorphous, cubic and hexagonal ice is 10° C. per hour from −180° C. to −150° C., 1° C. per hour from −150° C. to −70° C., and 10° C. per hour from −70° C. to −20° C.

Once the sample has reached 20° C., it can be sealed inside an appropriate container within the vacuum chamber and unloaded for subsequent storage. In one configuration, the sample is contained within a glass vial and sealed with a butylrubber lyophilization stopper at the end of cycle. More specific details of the operation of the molecular distillation dryer are given in U.S. Pat. No. 4,865,871.

Reconstitution

The freezing and drying of biological substances impart great physical stress upon the bonding forces which normally stabilize macromolecular conformation. Contributing to this destabilizing effect is the increase in concentration of electrolytes and possible pH changes as the solution freezes. As a consequence, modifications to the sample, including the dissolution of membrane structures, the inactivation of certain enzymes, and the denaturation of proteins, may result.

Studies with lactic dehydrogenase have shown that freezing and thawing cause dissociation of the tetrameric enzyme into subunits which is accompanied by a change in biological activity. The dissociation was found to be dependent on the ionic strength and pH during freezing.

Other studies investigating the quaternary structure of L-asparaginase demonstrated that this enzyme dissociated from the active tetramer to inactive monomers when freeze-dried. This monomeric state was found to be stabilized by reconstitution of the dried enzyme with buffers of high pH and high ionic strength. However, the dissociation was shown to be completely reversible on reconstitution at neutral pH and low ionic strength. The effect of pH on the other hand may induce changes in the three dimensional structure resulting in subunits conformationally restrained from reassociation.

These studies indicate the importance of determining optimal pH and ionic strength conditions of not only the formulation used in the cryopreservation protocol, but also the reconstitution solution. In this way, maximal sample activity and stability may be obtained.

Other variables of reconstitution such as vapor phase rehydration or temperature may also be important to the retention of activity following freezing and drying. Other workers in the field have demonstrated a marked difference in proliferative response to lectins depending on the temperature of rehydration or whether samples were reconstituted by vapor phase. Improved responses to lectins were noted when the freeze-dried lymphocytes were rehydrated at dry ice temperatures and then allowed to warm. This gradual method of reconstitution reduced the osmotic stress induced by sudden rehydration.

Storage Considerations

Sublimation of water from a frozen sample has been an excellent method for preserving the active components of biological material. However, the optimal preservation of activity with long-term stability requires critical control of the drying process and storage conditions. Following the removal of free or unbound sample water, the process of secondary drying proceeds in which structurally bound water is removed. Bound water is intimately associated with the maintenance of protein conformation. Thus, the amount of water remaining in the dried sample, known as the residual moisture content, is a significant variable in the drying process, as it affects both the survival and stability of the sample.

Residual moisture content is expressed as the "percentage residual moisture" and is equated to the weight (gm) of residual water per unit weight (gm) of original sample.

It is generally agreed that biological materials dried by vacuum sublimation of ice show increased stabilization when dried to optimum contents of residual moisture. Materials which have been under or overdried, i.e., to moisture contents that are above or below the optimum, will show increased deterioration.

Although the optimal residual moisture content will vary depending on the particular dried sample, certain stability problems can be expected when the levels of moisture are suboptimal. Overdrying a sample, i.e., residual moisture contents less than 1–2% without using a dry stabilizer, generally results in removal of nearly all structured water allowing saturation or blocking of exposed hydrophilic sites of proteins by oxidation. This oxidation causes degradation with a corresponding decrease in the biological activity. On the other hand, residual moisture contents of greater than 5% generally are indicative of underdrying where sufficient amounts of "free water" remain in the sample which could contribute to transconformation of the protein. The resulting rearrangements of the polypeptide chains shift from the typical ordered arrangement of the native protein to a more disordered arrangement. These protein perturbations can result in poor long-term stability of the dried product.

Successful long-term storage requires sample drying to optimal levels of residual moisture. Inadequate drying of biological samples and its consequences have been shown in the literature. Maximal stability of suspensions of influenza virus dried by sublimation of water in vacuo occurred at a residual moisture content of approximately 1.7%. Under or over drying to sub-optimal water content resulted in the degradation of the virus suggesting that varying amounts of free and bound water in a dried sample have an effect upon protein structure and activity.

To maximize sample stability and satisfy regulatory requirements for the preparation of dried pharmaceuticals or reagents, it is essential that the residual moisture content be determined following sample drying.

Several methods are available to measure residual moisture contents;

1. Gravimetric (Heating Method)—A known quantity of dried product is heated and the weight loss can be equated with water content.

2. Chemical Assay—This method is based on the reaction between water and free iodine in a mixture of pyridine, sulphur dioxide and methanol. The endpoint is detected coulometrically when free iodine is present. $H_2O+I_2+SO_2+ROH+3RN \rightarrow 2RNHI+RN+HSO_4R$ 3. Gas Chromatography Each of the methods has limitations and therefore, it is wise to not rely on any single method of moisture determination. Rather, multiple methods should be employed to validate the results.

Once dried to optimal residual moisture contents, the sample is still considered unstable when removed from the vacuum due to its hygroscopic nature and susceptibility to oxidation. Measures must be taken during storage to protect the sample from atmospheric rehydration and minimize exposure to oxygen. Such protection is essential to the maintenance of the sample's long-term stability.

Evidence in the literature indicates that the gaseous condition under which the samples are sealed, as well as the storage temperature, effects the long-term stability of the sample. It has been demonstrated in a study comparing different gases and storage temperatures, that maximum stability of influenza virus was obtained when samples were stored under helium or hydrogen gas at low temperature (−20° C.). Sealing under other gases or vacuum at different storage temperatures resulted in varying levels of stability. The inventors postulate that those conditions which most effectively limit oxygen contact with the sample, markedly improve biological activity by reducing oxidation of exposed hydrophilic sites at the protein surface. Appropriate storage parameters, i.e., temperature, and sealing under gas or vacuum are important to obtain long-term sample stability.

Protectants

Cryopreservation is accomplished by a combination of cryoprotectant and optimum cooling rate. The aim is to minimize the concentration of cryoprotectant required, and therefore its toxicity, and to also minimize the rate of cooling required to achieve the appropriate ice phases in the sample.

Although activity in the development of the process of this invention has been primarily directed to the cryopreservation and dry stabilization of biological samples such as viruses, cultured cells and erythrocytes, the process is not so limited. Some of the cryoprotectants and dry protectants that have been used successfully in the method of this invention and which allow the retention of biological activity following cooling and drying are described in the following examples:

EXAMPLE 1

Preservation and Storage of Mammalian Cultured Cells

1. NCTC 929 cells were resuspended in LISP at $2.5 \times 10^5$ cells/ml.
2. The cells were then nebulized with an ultrasonic nebulizer (25 kHz nozzle) at 1.5 watts, 6 ml/min flow rate, resulting in microdroplets having diameters of about 200 $\mu$m and cooled to a temperature below $-160°$ C., using the device described above.
3. Approximately 2 ml aliquots of the cells (based on initial liquid volume) were collected and placed in glass vials, and were then dried in a molecular distillation dryer.
4. Following drying, the vials were sealed under vacuum in the dryer and the vacuum was reversed with dry nitrogen gas.
5. Following storage at 4° C. for 3 days, a vial was opened under ambient conditions and the dry cells were transferred into a cell culture dish containing 250 $\mu$l of a vitrification solution ($VS_1$) comprised of:

| | |
|---|---|
| DMSO | 0.5M |
| Propylene glycol | 0.5M |
| 2-3 butanediol | 0.25M |
| Raffinose | 10% (w/v) |
| Trehalose | 6% (w/v) |
| Sucrose | 6% (w/v) |
| PVP (Av. M.W.-40,000) | 12% (w/v) |
| Dextran (Av. M.W.-70,000) | 12% (w/v) |

6. The vitrification solution was then diluted in steps at 10 minute intervals by adding normal cell culture medium. Each addition of medium resulted in the vitrification solution being diluted to the following concentrations: 70%, 50%, 25%, 12.5% and 1.25%.
7. After the final dilution, the culture dish was transferred to a 37° C., 5% CO2 incubator and left undisturbed for 2 weeks.

Results: Following full processing, including nebulization, rapid freezing, molecular distillation drying, and rehydration, the cultured cells showed an intact electron microscopic appearance with distinct cytoplasm and nucleus and defined cellular organelles. Selected cells showed trypan blue exclusion and fluoresce green with acridine orange and propidium iodide. Eleven colonies grew from the rehydrated cells.

EXAMPLE 2

Preservation and Storage of Mammalian Cultured Cells

1. NCTC 929 cells were resuspended in LISP and 1% glycerol at $2.5 \times 10^5$ cells/ml. The cells were then incubated at room temperature for 20 minutes, cooled on ice for 20 minutes, spun down in a refrigerated centrifuge (4° C., 5 min, 1000 rpm), aspirated to remove the supernatant and resuspended to the original volume in cold (4° C.) LISP buffer.
2. The cell suspension was then nebulized with a 25 kHz nozzle set at 1.5 watts with a flow rate of 6 ml/min using the modified Sonotek device described above.
3. The nebulized microdroplets were frozen in the microdroplet cryofixation device described in the specification.
4. The frozen microdroplets were collected and dried in a Virtis bench top freeze dryer which had been modified by placing a $-80°$ C. condenser surface near the sample.
5. The dry cells were sealed under vacuum, unloaded from the dryer and stored at 4° C. for 3 days.
6. A dry sample vial was allowed to come to room temperature and half of the sample were rehydrated in 250 $\mu$l of each of the following:
   a. 25% dextran (mol. wt. 480,000) in 0.2 M Tris-HCl, pH 8.3.
   b. Saturated mannitol in 0.2 M Tris-HCl, pH 8.3.
7. The cells were then diluted 8 fold in 4 steps with NCTC 135 medium with 10% horse serum and standard tissue culture concentrations of penicillin and streptomycin.
8. Half of each suspension was then plated on a petri dish while the other half was spun down, resuspended in NCTC 135 medium with 10% horse serum, penicillin and streptomycin, and then plated.
9. Cell growth was evaluated by counting colonies 2 weeks later.
10. From the approximately $2.5 \times 10^5$ cells, 13 total colonies were generated:
    a. 1 colony from the sample rehydrated in dextran and then plated;
    b. 4 colonies from the sample rehydrated in dextran, resuspended in NCTC 135 medium and then plated;
    c. 8 colonies from the sample rehydrated in mannitol and then plated; and
    d. no colonies from the last sample which became contaminated during processing.

EXAMPLE 3

Preservation and Storage of Mammalian Cultured Cells

1. NCTC 929 cells were resuspended in LISP and 1% horse serum at $2.5 \times 10^5$ cells/ml.
2. The cell suspension was then nebulized with a 25 kHz nozzle set at 1.5 watts with a flow rate of 6 ml/min using the modified Sonotek device described above.
3. The nebulized microdroplets were frozen in the microdroplet cryofixation device described in the specification.
4. The frozen microdroplets were collected and dried in a Virtis bench top freeze dryer which had been modified by placing a $-80°$ C. condenser surface near the sample.
5. The dry cells were sealed under vacuum, unloaded from the dryer and stored at 4° C. for 3 days.

6. A dry sample vial was allowed to come to room temperature and rehydrated in 250 µl of a 1:1 mixture of 25% dextran (M.W. 480,000) and saturated mannitol in 0.2 M Tris-HCl, pH 8.3.
7. The cells were then diluted 8 fold in 4 steps with NCTC 135 medium with 10% horse serum and standard tissue culture concentrations of penicillin and streptomycin.
8. Approximately half of the cells were then plated on a petri dish while the other half was spun down, resuspended in NCTC 135 medium with streptomycin, then plated.
9. Cell growth was evaluated by counting colonies 2 weeks later.
10. From the approximately $2.5 \times 10^5$ cells, 80 total colonies were generated, 40 from each of the suspensions.

EXAMPLE 4

Preservation and Storage of Human Erythrocytes

Fresh human erythrocytes were obtained by venipuncture and collected in ACD anticoagulant in the ratio of 1:10 with whole blood. The blood sample was then centrifuged at 2000 g for 10 minutes and the supernatant removed.

The packed red cell sample was then diluted to a 5–10% hematocrit using a buffer (Adsol) consisting of 2.2% dextrose, glucose, 0.9% sodium chloride, 0.75% mannitol and 0.027% adenine.

Once obtained and isolated, the following steps were employed to preserve and store the erythrocyte sample.

1. The erythrocyte suspension was prepared as three cryosolutions which consisted of the following:
   a. cells added to buffer alone.
   b. cells which were pretreated at 22° C. with one percent glycerol. Following a 20 minute incubation, the cells were cooled to 4° C. on ice. When the cells had equilibrated to 4° C., they were centrifuged at 4° C. for 10 minutes at 2000 g. The supernatant was then removed and the cells resuspended in a 4° C. solution consisting of 1% dextran (average MW 40,000–70,000) in buffer, to a final hematocrit of 5–10%.
   C. cells which were treated with a 5% vitrification solution ($VS_1$ discussed above, diluted 20:1) composed of 0.025M dimethylsulfoxide, 0.025M propylene glycol, 0.0125M 2-3 butane diol, 0.5% raffinose, 0.3% trehalose, 0.3% sucrose, 0.6% polyvinylpyrrolidine and 0.6% dextran.
2. The cryosolutions were then nebulized at a flow rate of 6 mls per minute using the ultrasonic nebulizer described above at 1.5–2.5 watts and 25–60 kHz.
3. The nebulized cryosolution was rapidly frozen without contact with liquid cryogen using the internally cooled cryogenic surface described above.
4. The frozen sample was then collected and stored at temperatures below −160° C.
5. The erythrocyte samples were then dried by molecular distillation drying employing the methods described in U.S. Pat. No. 4,865,871.
6. The erythrocyte samples were stored under vacuum for up to 2 weeks.
7. The erythrocyte samples were then rehydrated by the addition of either:
   a. Adsol buffer; or
   b. 40% dextran in buffer and serially diluted to 5% dextran in 6 steps by the addition of buffer. The erythrocyte sample was then centrifuged at 2000 g for 10 minutes and resuspended in buffer.
8. The erythrocyte samples were then assessed for morphology using phase contrast microscopy.
9. After storage and assay evaluations, the effectiveness of the various protocols were evaluated with the following results:
   Cryosolution: Adsol
   Rehydration: Adsol
   Morphology: 90% small cells, 10% ghost cells
   Cryosolution: Adsol
   Rehydration: 40% Dextran
   Morphology: 100% intermediate cells
   Cryosolution: 5% $VS_1$
   Rehydration: Adsol
   Morphology: 20% small cells, 80% ghost cells
   Cryosolution: 5% $Vs_1$
   Rehydration: 40% Dextran
   Morphology: 20% small cells, 30% intermediate cells, 40% large cells and 10% ghost cells
   Cryosolution: 1% intracellular glycerol, 1% extracellular Dextran
   Rehydration: Adsol
   Morphology: 50% small cells, 45% intermediate cells, 5% ghost cells
   Cryosolution: 1% intracellular glycerol, 1% extracellular Dextran
   Rehydration: 40% Dextran
   Morphology: 5% small cells, 95% intermediate cells

EXAMPLE 5

Preservation and Storage of Oral Polio Vaccine (OPV)

Oral polio vaccine (OPV) is composed of three serotypes of live but attenuated poliomyelitis virus. It is one of the two commonly used vaccines for the prevention and treatment of the crippling disease of poliovirus. Methods for obtaining and isolating live, attenuated polio virus are known to those skilled in the art of virology.

The effectiveness of the present invention was demonstrated by the following experiments:

1. A trivalent preparation of oral polio vaccine (OPV) was obtained from the manufacturer and stored at −80° C.
2. Immediately prior to processing, the preparation was thawed in a 37° C. water bath. The preparation was then desalted by ultrafiltration using a stirred cell device.
3. The desalted OPV samples were then resuspended in the following solutions until fully suspended to form a cryosolution and allowed to incubate at room temperature for 30 minutes.
   a. 1M MES buffer alone, pH 8.5
   b. 1M Tris buffer alone, pH 8.5
   c. 250mM Trehalose in 1M Tris buffer, pH 8.5
4. Following incubation, the cryosolutions were rapidly frozen using the nebulizing device previously described. For each of the cryosolutions, 500 µl of nebulized sample was collected into small, (5 cc) freeze drying vials maintained at cryogenic temperatures.

Butyl rubber lyophilization stoppers were placed in the openings of the vials.

5. The nebulized samples were then placed into a liquid nitrogen cooled sample holder and loaded into a molecular distillation dryer and dried by molecular distillation drying.
6. Upon reaching 20° C., the vials were sealed within the dryer under vacuum.
7. The dried samples were removed from the dryer and stored at room temperature for approximately two weeks before being assayed.

8. At the time of assay, the OPV samples were reconstituted with 500 μl of distilled water by injection through the lyophilization stopper.

9. The OPV samples were assayed for viral titers of each serotype utilizing standard methods.

10. After assay evaluations, the effectiveness with respect to viral activity was assessed in duplicate and expressed as $TCD_{50}$.

| Cryosolution | Serotype I | Serotype II | Serotype III |
|---|---|---|---|
| MES buffer alone | 4.45 | 4.45 | 4.45 |
| Tris buffer alone | 5.41 | 4.94 | 6.08 |
| 250 mM Trehalose in Tris buffer | 4.87 | 4.60 | 4.59 |
| Control | 7.02 | 6.18 | 7.13 |

Although the preferred embodiment of the apparatus used in the practice of this invention has been described hereinabove in some detail, it should be appreciated that a variety of embodiments will be readily apparent to a person designing cryopreparation apparatus for a specific end use. The description of the apparatus of this invention is not intended to be limiting on this invention, but is merely illustrative of the preferred embodiment.

While the compositions and methods for sample preservation and storage have been described in terms of preferred embodiments, it will be apparent to those of skill in the art that variations and modifications may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein such that the same or similar results would be achieved. The examples presented above describe methods for preserving and storing microscopic biological materials in suspension. Substitutes and modifications apparent to those skilled in the art are deemed to be within the spirit, scope and concept of this invention as defined by the appended claims.

What is claimed is:

1. A cryoprotective solution selected from the group consisting of:

(1) a mixture of 0.5 molar dimethyl sulfoxide, 0.5 molar propylene glycol, 0.25 molar 2,3 butanediol, 1.0 molar proline, 2.5% raffinose and 15% polyvinylpyrrolidone;

(2) a mixture of 0.5 molar dimethyl sulfoxide, 0.5 molar propylene glycol, 0.25 molar 2,3 butanediol, 10% raffinose, 6% trehalose, 6% sucrose, 12% polyvinylpyrrolidone and 12% dextran; and (3) a mixture of 0.5 molar dimethyl sulfoxide, 0.5 molar propylene glycol, 0.25 molar 2,3 butanediol, 2.5% raffinose, 12% sucrose, 15% polyvinylpyrrolidone and 12% dextran.

* * * * *

UNITED STATES PATENT AND TRADEMARK OFFICE
CERTIFICATE OF CORRECTION

PATENT NO. : 6,194,136 B1
DATED : January 27, 2001
INVENTOR(S) : Stephen A. Livesey, et al.

It is certified that error appears in the above-identified patent and that said Letters Patent is hereby corrected as shown below:

In Column 10, Line 62, in the equation delete $10_{28}$ and insert -$10^{28}$ -

In Column 10, Line 67, in the equation, delete $10_{12}$ and insert -$10^{12}$ -

Signed and Sealed this

Fifth Day of June, 2001

Attest:

NICHOLAS P. GODICI

*Attesting Officer*

*Acting Director of the United States Patent and Trademark Office*